United States Patent
Muslih (10) Patent No.: US 10,074,198 B2
(45) Date of Patent: Sep. 11, 2018

(54) METHODS AND APPARATUSES FOR IMAGE PROCESSING AND DISPLAY

(71) Applicant: Change Healthcare Holdings, LLC, Nashville, TN (US)

(72) Inventor: Faisal Muslih, Coquitlam (CA)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 101 days.

(21) Appl. No.: 15/085,526

(22) Filed: Mar. 30, 2016

(65) Prior Publication Data

US 2017/0287174 A1    Oct. 5, 2017

(51) Int. Cl.
G06T 7/00    (2017.01)
G06T 11/00   (2006.01)
G06T 5/50    (2006.01)

(52) U.S. Cl.
CPC .............. *G06T 11/005* (2013.01); *G06T 5/50* (2013.01); *G06T 2207/20221* (2013.01); *G06T 2207/30004* (2013.01)

(58) Field of Classification Search
CPC ..................... G06T 11/005; G06T 5/50; G06T 2207/20221; G06T 2207/30004; G06T 7/11; G06T 7/0012; G06T 2207/20128
See application file for complete search history.

(56) References Cited

U.S. PATENT DOCUMENTS

| | | | |
|---|---|---|---|
| 2005/0031202 A1* | 2/2005 | Accomazzi | G06K 9/346 382/173 |
| 2012/0197619 A1* | 8/2012 | Namer Yelin | G06F 19/3437 703/11 |
| 2013/0121549 A1* | 5/2013 | Pekar | G06T 7/0012 382/128 |

* cited by examiner

*Primary Examiner* — Jon Chang
(74) *Attorney, Agent, or Firm* — Alston & Bird LLP (57) ABSTRACT

A method, apparatus and computer program product provide improved image processing techniques. An example of a method includes receiving a source image, programmatically identifying a plurality of anatomical elements within the source image through use of a computer vision technique, determining a first region of the source image corresponding to a first anatomical element, determining a second region of the source image corresponding to a second anatomical element, applying at least one first configuration setting to the first region, applying at least one second configuration setting to the second region, the at least one second configuration setting different from the at least one first configuration setting, and generating a merged image, wherein the merged image comprises the first region as visualized according to the at least one first configuration setting and the second region as visualized according to the at least one second configuration setting.

16 Claims, 5 Drawing Sheets

METHODS AND APPARATUSES FOR IMAGE PROCESSING AND DISPLAY

TECHNOLOGICAL FIELD

Example embodiments of the present invention relate generally to methods, systems, and computer readable storage media for processing medical images and, more particularly, to methods, systems, and computer readable media for generating merged images having multiple regions associated with different configuration settings.

BACKGROUND

Clinical analysis and diagnosis using medical images requires careful control and manipulation of view settings associated with particular image types. X-rays, ultrasounds, computerized tomography (CT) scans, and other medical image capture techniques require the use of carefully selected view configuration settings based upon the image capturing technique (e.g., the particular technology or device used to capture the image), the viewing angle (e.g., a front view or lateral view of the patient's anatomy), the particular portion of patient anatomy being imaged (e.g., torso, head, arm, leg), and the particular anatomical element desired to be viewed (e.g., viewing an image to diagnose a problem in the patient's lung may require different image view configuration settings than viewing a patient's heart). To view a scan of the patient's thoracic cavity, for example, a clinician may need to view the same image with a plurality of different configuration settings to properly view all of the anatomical elements within the same captured image portion. For example, an image may include both the patient's heart and lungs, but brightness and contrast settings used to visualize the lungs may result in a loss of visual fidelity in a region of the image corresponding to the heart, and vice-versa.

Accordingly, in order to properly clinically analyze images that include anatomical elements that, for proper visualization, require the use of multiple different configuration settings, the clinician often must flip back and forth between different viewer configurations to view the same image. Many clinicians address this problem by opening multiple viewports with different viewer configuration settings, but this solution is inadequate as it requires shifting their physical view across multiple different images.

Through applied effort, ingenuity, and innovation, the inventor has solved many of these identified problems by developing a technical solution that is embodied by the present invention, which is described in detail below.

BRIEF SUMMARY

Methods, apparatuses and computer program products are therefore provided according to example embodiments of the present invention in order to provide merged images having a plurality of regions associated with different viewer configuration settings. These merged images may exist as separate images, or within a viewport defined within a medical image viewing application. Regions are defined based on the presence of particular anatomical elements, such that each region is associated with one or more anatomical elements. Anatomical elements may be detected by various processes and algorithms, and regions within the image are defined to encompass or otherwise be associated with those anatomical elements. Embodiments may further include a database or table comprising configuration settings for particular anatomical elements, such that detected anatomical elements are mapped to configuration settings stored in the database, and those configuration settings are applied to regions of the image corresponding to the anatomical elements.

An example of an embodiment includes a method for implementing improved image processing techniques. The method includes receiving a source image, programmatically identifying a plurality of anatomical elements within the source image through use of a computer vision technique, determining a first region of the source image corresponding to a first anatomical element of the plurality of anatomical elements, determining a second region of the source image corresponding to a second anatomical element of the plurality of anatomical elements, applying at least one first configuration setting to the first region, applying at least one second configuration setting to the second region, the at least one second configuration setting different from the at least one first configuration setting, and generating a merged image, wherein the merged image comprises the first region as visualized according to the at least one first configuration setting and the second region as visualized according to the at least one second configuration setting.

In some embodiments, the method includes determining a type of the first anatomical element using the computer vision technique, and selecting the at least one first configuration setting based at least in part on the type of the first anatomical element. Selecting the at least one first configuration setting based at least in part on the type of the first anatomical element comprises looking up the type of the first anatomical element in a database of configuration settings. The method may also include displaying the merged image in an interface, wherein the interface comprises at least one interface control associated with each of the first region and the second region, receiving a selection of an interface control associated with the first region, and in response to receiving the selection of the interface control associated with the first region, applying the at least one configuration setting to the entire merged image. The at least one first configuration setting may include at least one of a brightness setting, a contrast setting, or a color correction setting. Generating the merged image may include outputting the merged image via a viewer application. The image may be output via a Picture Archiving and Communications System. The source image may be a Digital Imaging and Communications in Medicine image. The method may include storing the merged image in a memory. The method may include storing data defining the first region and the second region and the data defining the configuration settings associated with the first region and the second region as metadata for the merged image.

Another example of an embodiment includes an apparatus for implementing improved image processing techniques. The apparatus includes a processor and a memory. The memory stores instructions that are executed by the processor to configure the apparatus to receive a source image, programmatically identify a plurality of anatomical elements within the source image through use of a computer vision technique, determine a first region of the source image corresponding to a first anatomical element of the plurality of anatomical elements, determine a second region of the source image corresponding to a second anatomical element of the plurality of anatomical elements, apply at least one first configuration setting to the first region, apply at least one second configuration setting to the second region, the at least one second configuration setting different from the at least one first configuration setting, and generate a merged image, wherein the merged image comprises the first region as visualized according to the at least one first configuration setting and the second region as visualized according to the at least one second configuration setting.

In some embodiments, the apparatus is further configured to determine a type of the first anatomical element using the computer vision technique, and select the at least one first configuration setting based at least in part on the type of the first anatomical element. Selecting the at least one first configuration setting based at least in part on the type of the first anatomical element may include looking up the type of the first anatomical element in a database of configuration settings. The apparatus may be further configured to display the merged image in an interface, wherein the interface comprises at least one interface control associated with each of the first region and the second region, receive a selection of an interface control associated with the first region, and in response to receiving the selection of the interface control associated with the first region, apply the at least one configuration setting to the entire merged image. The at least one first configuration setting may include at least one of a brightness setting, a contrast setting, or a color correction setting. Generating the merged image may include outputting the merged image via a viewer application. The image may be output via a Picture Archiving and Communications System. The source image may be a Digital Imaging and Communications in Medicine image. The apparatus may be further configured to store the merged image in a memory.

Another example of an embodiment includes a non-transitory computer readable storage medium comprising instructions that, when executed by a processor, cause the processor to implement improved image processing techniques. The instructions configure the processor to receive a source image, programmatically identify a plurality of anatomical elements within the source image through use of a computer vision technique, determine a first region of the source image corresponding to a first anatomical element of the plurality of anatomical elements, determine a second region of the source image corresponding to a second anatomical element of the plurality of anatomical elements, apply at least one first configuration setting to the first region, apply at least one second configuration setting to the second region, the at least one second configuration setting different from the at least one first configuration setting, and generate a merged image, wherein the merged image comprises the first region as visualized according to the at least one first configuration setting and the second region as visualized according to the at least one second configuration setting.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having thus described certain embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Introduction

A method, apparatus and computer program product are provided in accordance with example embodiments of the present invention to provide improved systems for processing and displaying images. As noted above, the inventor has identified that present systems for visualizing medical images are inadequate. To address these problems and other problems, the inventors have developed a system that generates merged images that include multiple regions that are displayed according to configuration settings associated with anatomical elements identified within those multiple regions. In this manner, embodiments of the present invention are operable to identify regions of a source image associated with particular anatomical elements, select configuration settings for those regions based at least in part on those identified anatomical elements, and generate a merged image such that the regions associated with each anatomical element have corresponding configuration settings. These configuration settings may include, for example, brightness levels, contrast levels, color correction settings, and the like.

For the purposes of this disclosure, the terms "source image" and "source medical image" should be understood to refer to any source set of image data, including but not limited to images stored in a Digital Imaging and Communications in Medicine (DICOM) format. The source medical image may have a set of configuration settings applied for viewing, or the source medical image may refer to an image prior to the application of configuration settings or other adjustments applied within a viewer application.

For the purposes of this disclosure, the terms "configuration settings," "viewer configuration settings," and "view configuration settings," should be understood to refer to settings or changes that are applied to a set of image data to display that image within a viewer application. The term should be understood to include brightness, contrast, color balance, and other settings that may be applied to the image to control the manner in which that image is displayed within the viewer application.

For the purposes of this disclosure, the term "merged image" should be understood to refer to an output image including image data that is generated from a source image having different configuration settings applied to two or more regions identified within the source image. The merged image may include additional data identifying the particular regions, the anatomical elements identified within the image, and/or the configuration settings used to generate the image, though the definition of merged image should also be understood to encompass images generated using a plurality of configuration settings but which do not include such data. It should be appreciated that the term "merged image" is used to refer to an image that is generated through the merger of different configuration settings applied to different regions of the image. While some source images may include a series of images processed together (e.g., CT scan images that layer a plurality of images over one another), such an image would not qualify as a "merged image" under the definition used throughout this application unless those series of images also included two or more regions with different configuration settings applied.

For the purposes of this disclosure, the term "anatomical element" should be understood to refer to any feature of human anatomy, surgical instrument, implant, or the like that may be identified within a medical image.

For the purposes of this disclosure, the term "medical image" refers to any image captured as part of a medical imaging operation including, without limitation, CT scans, x-rays, ultrasounds, magnetic resonance imaging (MRI) operations, positron emission tomography (PET) scans, or the like.

Exemplary Client Apparatus

Figure 1:
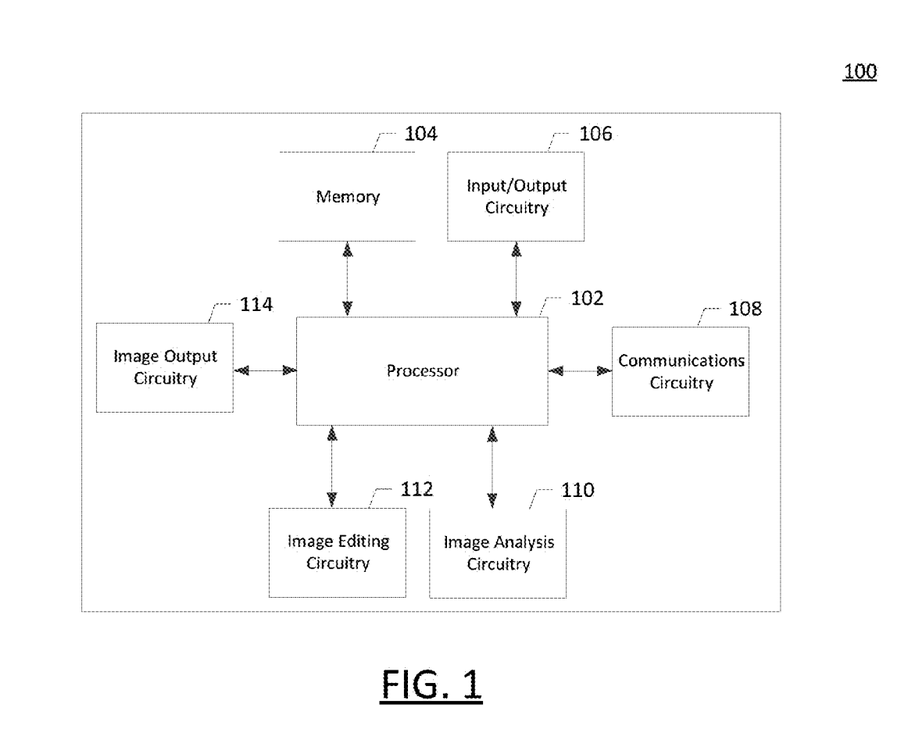
FIG. 1 is a block diagram of an apparatus for providing improved image processing and display in accordance with some embodiments of the present invention.

FIG. 1 illustrates a block diagram of an apparatus 100 in accordance with some example embodiments. The apparatus 100 may be any computing device capable of implementing improved techniques for image processing and visualization as described herein. For example, the apparatus 100 may be implemented as a computing device executing one or more applications for receiving, processing, and outputting images. The apparatus 100 implements hardware and software that serves to receive source image data, identify regions of the source image that correspond to anatomical elements, determine configuration settings for those regions based on the determined anatomical elements, apply the determined configuration settings to their corresponding regions, and generate a merged image that represents the application of the determined configuration settings to the source image.

The apparatus 100 may be implemented as a standalone or rack-mounted server, a desktop computer, a laptop computer, a personal digital assistant, a tablet computer, a netbook computer, a mobile device, a Picture Archive and Communications System (PACS) workstation or the like. Accordingly, it will be appreciated that the apparatus 100 may comprise devices, hardware, and the like configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

As illustrated in FIG. 1, an apparatus 100 may include a processor 102, a memory 104, input/output circuitry 106, communications circuitry 108, image analysis circuitry 110, image editing circuitry 112, and image output circuitry 114. The apparatus 100 may be configured to utilize the source image described below with respect to FIG. 3A, generate the merged image described below with respect to FIG. 3B, and to execute the operations described below with respect to FIGS. 2 and 4. Although these components 102-114 are described with respect to functional limitations, it should be understood that the particular implementations necessarily include the use of particular hardware. It should also be understood that certain of these components 102-114 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, "circuitry" includes processing circuitry, storage media, network interfaces, input/output devices, and/or the like. In some embodiments, other elements of the apparatus 100 may provide or supplement the functionality of particular circuitry. For example, the processor 102 may provide processing functionality, the memory 104 may provide storage functionality, the communications circuitry 108 may provide network interface functionality, and the like, such that each of the circuitries may be formed by other circuitry components of the apparatus 100.

In some embodiments, the processor 102 (and/or co-processor or any other processing circuitry assisting or otherwise associated with the processor) may be in communication with the memory 104 via a bus for passing information among components of the apparatus. The memory 104 may be non-transitory and may include, for example, one or more volatile and/or non-volatile memories. In other words, for example, the memory may be an electronic storage device (e.g., a computer readable storage medium). The memory 104 may be configured to store information, data, content, applications, instructions, tables, data structures, or the like, for enabling the apparatus to carry out various functions in accordance with example embodiments of the present invention.

The processor 102 may include various processing devices and may, for example, include one or more processing devices configured to perform independently from one another. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 102 may be configured to execute instructions stored in the memory 104 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, and the instructions may specifically configure the processor to perform the algorithms and/or operations described herein when the instructions are executed.

In some embodiments, the apparatus 100 may include input/output circuitry 106 that may, in turn, be in communication with the processor 102 to provide output to the user and, in some embodiments, to receive an indication of a user input. The input/output circuitry 106 may comprise a user interface and may include a display and may comprise a web user interface, a mobile application, a client device, a kiosk, or the like. In some embodiments, the input/output circuitry 106 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 104, and/or the like). The input/output circuitry 106 may provide a mechanism for display of a merged image (e.g., via a monitor or other display), and receiving input related to an image viewing interface (e.g., a mouse, keyboard, or the like).

The communications circuitry 108 may be any means such as a device or circuitry embodied in either hardware or a combination of hardware and software that is configured to receive and/or transmit data from/to a network and/or any other device, circuitry, or module in communication with the apparatus 100. In this regard, the communications circuitry 108 may include, for example, a network interface for enabling communications with a wired or wireless communication network. For example, the communications circuitry 108 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The image analysis circuitry 110 includes hardware configured to receive and/or generate a source image and analyze the image to identify regions of the image associated with particular anatomical elements. In this regard, the image analysis circuitry 110 may include one or more application specific interface circuits designed to or a configured processor, such as the processor 102, programmed with one or more image analysis algorithms to identify regions of a source image that correspond to one or more anatomical elements. This identification process may include associating particular pixels or borders identifying pixel regions with those particular anatomical elements. For example, the image analysis circuitry 110 may implement or utilize image atlasing algorithms, image segmentation capabilities, or the like, such as the various image analysis libraries offered by Toshiba Medical Systems.

The image editing circuitry 112 includes hardware configured to adjust configuration settings or otherwise edit a source image to produce a merged output image. In this regard, the image editing circuitry 112 includes one or more ASICs or configured processors that are configured to apply configuration settings, such as brightness and/or contrast settings, to a source image. For example, the image editing circuitry 112 may apply the brightness and contrast settings to adjust the intensity of particular pixels within the source image. The particular brightness and contrast settings may be selected for each pixel based on whether that pixel corresponds to a region of the image in which a particular anatomical element was identified by the image analysis circuitry 110. The image editing circuitry 112 may, in some embodiments, implement part or all of an image viewing application such that the image editing circuitry edits a set of data within the viewer application to implement the configuration settings. Alternatively, in some embodiments the image editing circuitry 112 may generate a merged image as output to be stored for use by an image viewing application implemented externally to the image editing circuitry 112. In this manner, the merged image may be stored for use with any image viewer that is capable of accessing the archive in which the image is stored.

The image output circuitry 114 includes hardware configured to display a merged image such as generated by the image editing circuitry 112. The image output circuitry 114 includes one or more ASICs or configured processors that serve to implement an image viewer application that provides an interface for output of the merged image via a display or transmission to a remote computer for display. The image output circuitry 114 may include, for example, an image viewing component of a PACS workstation that allows a user to view the merged medical image in the context of a medical imaging study. The image output circuitry 114 may utilize one or more components of the input/output circuitry 106 to provide these functions.

As will be appreciated, any computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Exemplary Data Flow for Implementing Improved Image Processing Operations

Figure 2:
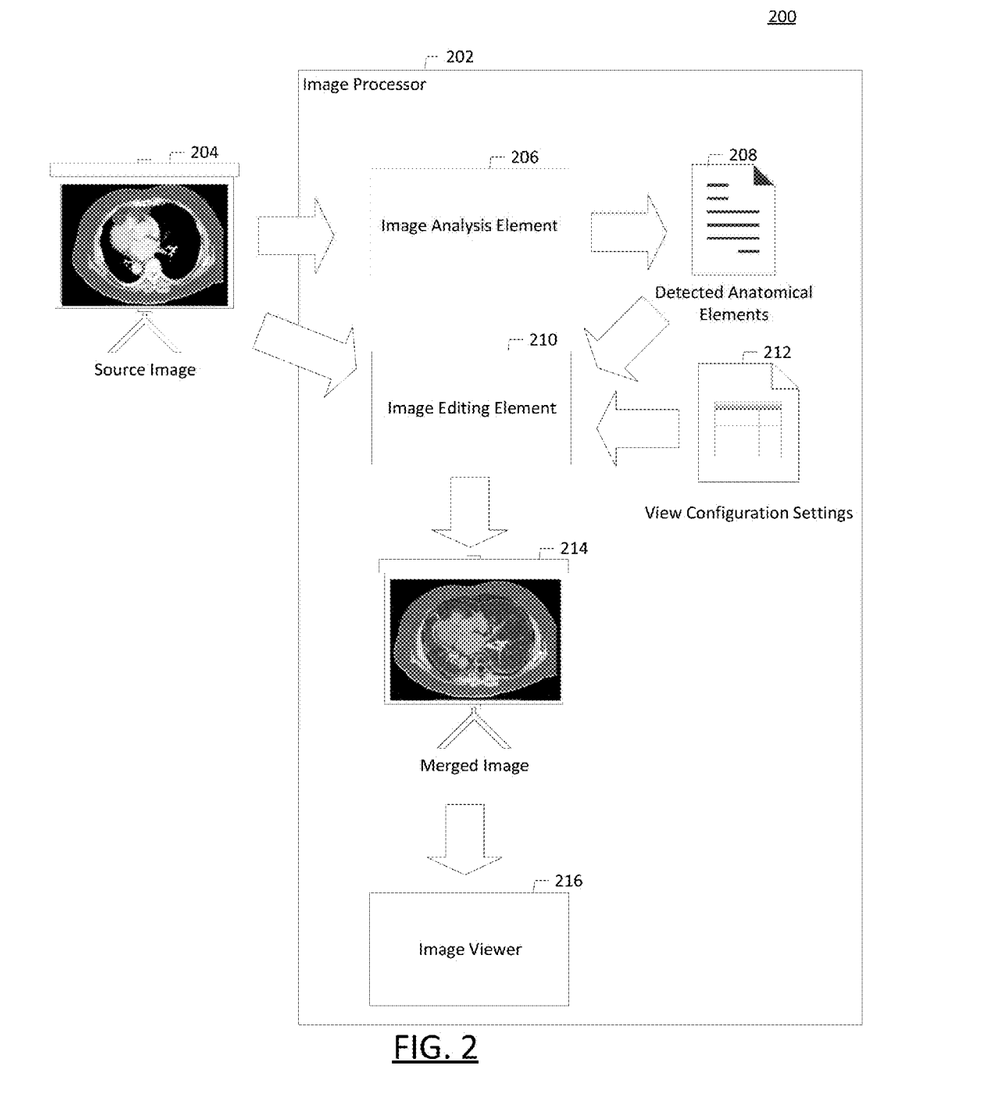
FIG. 2 is an illustration of a data flow for generating a merged medical image in accordance with some embodiments of the present invention.

FIG. 2 illustrates an example data flow 200 for implementing improved image processing operations for the generation of merged images in accordance with embodiments of the present invention. The data flow 200 illustrates the manner in which a source image 204 is processed by an image processor 202 to generate a merged image 214 for output via an image viewer 216. The image processor 202 may be implemented by an apparatus 100 as described above with respect to FIG. 1.

The source image 204 may be any set of image data that may be analyzed to detect anatomical elements. The source image 204 may, for example, be a DICOM image, a JPEG image, a GIF image, a PNG image, a TIF image, a RAW image, or any other image implemented according to any of a variety of formats, compression techniques, and the like. An example of a source image is described further below with respect to FIG. 3A. The source image 204 may be captured by a medical imaging process, received from a set of electronic health records, or from any other source or format.

The source image 204 is provided to an image analysis element 206. The image analysis element 206 analyzes the source image 204 to identify regions of the image that correspond to particular anatomical elements. The image analysis element 206 may be implemented by, for example, image analysis circuitry as described above with respect to FIG. 1. The image analysis element 206 may include, for example, one or more ASICs or processors programmed by algorithms for detection of anatomical elements within the source image, and determining which pixels or pixel regions correspond to those anatomical elements. The image analysis element 206 generates a set of detected anatomical elements 208.

The set of detected anatomical elements 208 includes a data structure or data structures that identify regions of the source image 204 and anatomical elements associated with those regions. The set of detected anatomical elements 208 may identify particular pixels associated with each anatomical element, regional boundaries (e.g., lines, line segments, or curves) associated with the region corresponding to each anatomical element, or the like. The set of detected anatomical elements 208 also includes the particular anatomical element identified. For example, a particular region may be identified as corresponding to a patient's heart, lungs, brain, bone, skin, or the like. In some embodiments, identification of the anatomical elements 208 may also include identification of instruments, implants, contrast media, or the like.

The set of detected anatomical elements 208 and the source image 204 are provided to an image editing element 210. The image editing element 210 also accesses a set of stored view configuration settings 212 that indicate particular configuration settings that are associated with particular anatomical elements. For example, the view configuration settings 212 may include particular brightness and contrast settings to be applied to regions of the image corresponding to a patient's heart, lungs, brain, bone, skin, or the like. For example, in some embodiments the configuration settings may include particular "Window" and "Level" units to represent brightness and contrast in Houndsfeld Units. For example, Soft Tissue regions may use a Window setting of 400 and a Level setting of 40, lung tissue regions may use a Window setting of 1600 and a Level setting of −550, and bone regions may use a Window setting of 2000 and a Level setting of 300.

The image editing element 210 may be implemented, for example, by the image editing circuitry 112 described above with respect to FIG. 1. The image editing element 210 may apply view configuration settings to each region of the source image 204 identified by the image analysis element 206 based on the settings for the anatomical elements detected within those regions as stored in the view configuration settings 212. As a result, the image editing element 210 may generate a merged image 214 that represents the application of these configuration settings to each region of the source image identified by the image analysis element 206. The image editing element 210 may store the merged image 214 or provide the merged image 214 directly to an image viewer 216 for output to a viewing interface. Storage of the merged image 214 may include storage of more than just the adjusted pixel data of the image. For example, some embodiments may store data identifying the particular regions of the image as identified by the image analysis element 206, the particular configuration settings applied to those regions, the anatomical elements detected within the image, or the like.

The image viewer 216 implements an interface suitable for viewing and accessing one or more images. For example, the image viewer 216 may be implemented by the image output circuitry 114 described above with respect to FIG. 1. The image viewer 216 may include an interface as a component of a PACS workstation for viewing the merged image 214. In some embodiments, the interface implemented by the image viewer 216 may also leverage additional aspects of the merged image 214 other than just output of the image as created by the image editing element 216. For example, embodiments may implement an interface that allows for selection of different regions of the image, such as via a cursor or touch screen. Upon selection of a region of the image, the interface may apply the configuration settings applied to that region to the entire image. For example, if a given source image depicts both a patient's heart and lungs, each with different applied configuration settings, selection of the region associated with the patient's lungs may apply the configuration settings to the entire image. In other embodiments, selection of a particular region may hide other regions of the image, or allow adjustment of configuration settings for that region alone, without affecting the other regions.

Exemplary Source and Merged Images

Figure 3A:
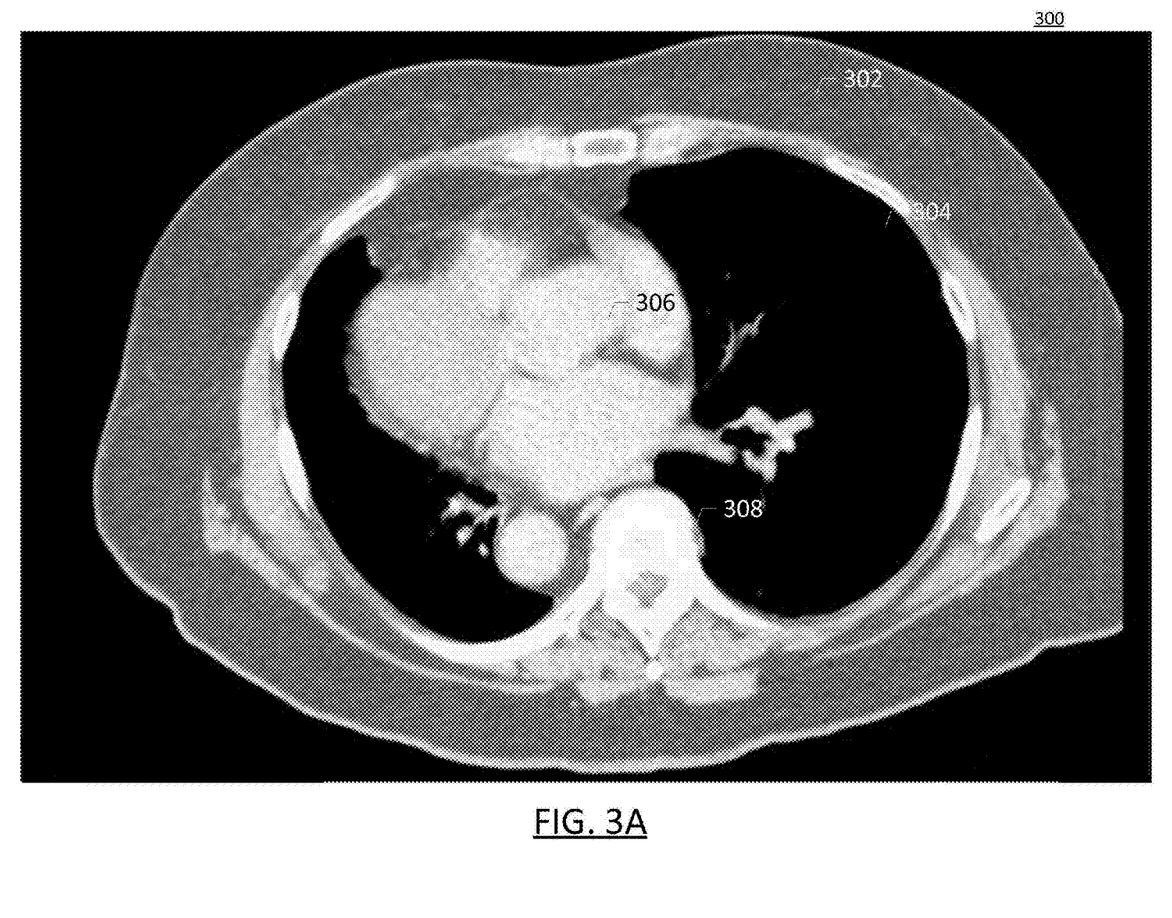
FIG. 3A is an illustration of a source medical image which may function as input to a system for providing improved image processing and display in accordance with some embodiments of the present invention.
Figure 3B:
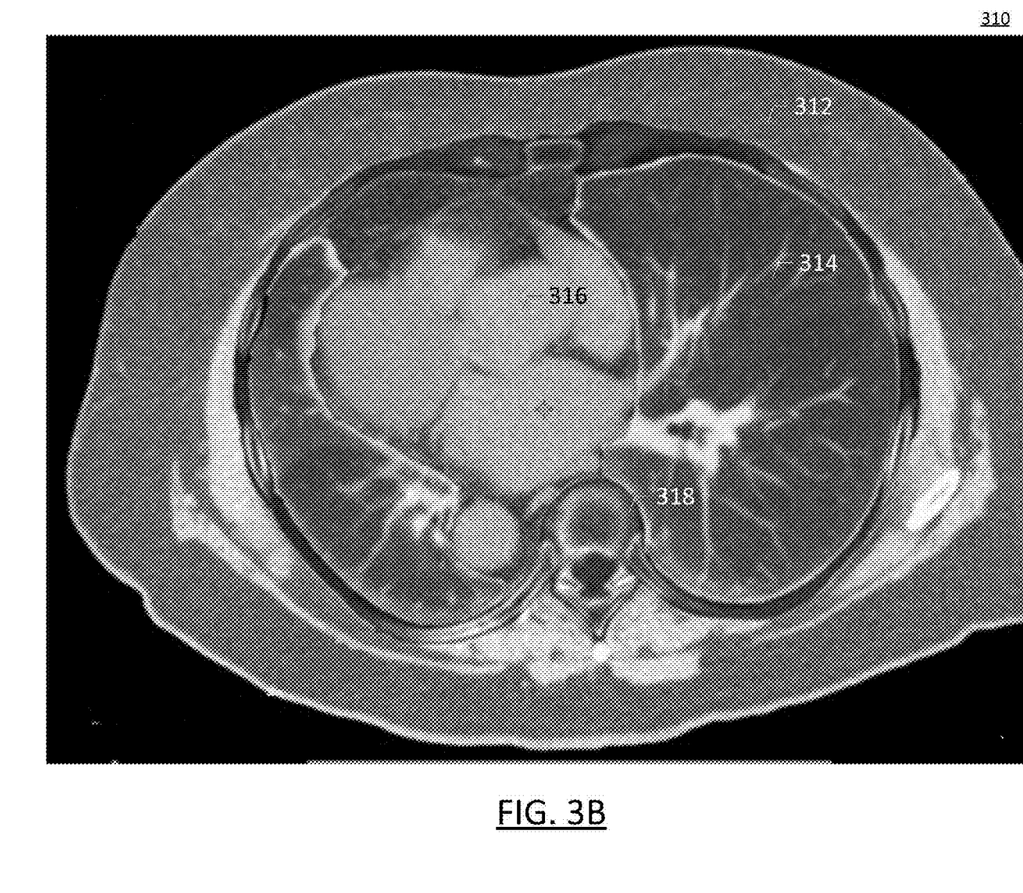
FIG. 3B is an illustration of a merged medical image function which may result as output from a system for providing improved image processing and display in accordance with some embodiments of the present invention.

FIGS. 3A and 3B illustrate a source image 300 and a merged image 310, respectively, as may be employed by embodiments of the present invention as part of an improved image processing and visualization operation. The source image 300 is a medical image, such as a CT scan image, that includes a view of a portion of a patient's thoracic cavity. The source image 300 in this example includes several different anatomical elements, including the patient's soft tissue 302 (e.g., skin and muscle), the patient's lungs 304, the patient's heart 306, and the patient's bone 308 (e.g., spine and rib cage). As can be seen from the source image 300, the present brightness and contrast settings applied across the image do not allow for proper visualization of certain portions of the patient's anatomy. For example, the brightness and contrast settings for the image result in an inability to discern detail within the patient's lungs 304. It should be appreciated however, that while elements of the source image are described as lacking appropriate brightness or contrast settings to illustrate the problems with improper settings, embodiments of the present invention also function with source images that do not have brightness/contrast settings applied as part of a visualization. In such scenarios, embodiments may interact directly with raw image data to identify anatomical elements as described herein.

An image analysis element, such as the image analysis element 206 described with respect to FIG. 2 or the image analysis circuitry 110 described with respect to FIG. 1 may serve to identify regions of the image corresponding to patient anatomical elements and the particular anatomical elements displayed therein. Image configuration settings may be selectively applied to regions of the image corresponding to the particular anatomical elements FIG. 3B illustrates an example of such a merged image 310 that incorporates multiple regions having different configuration settings.

The merged image 310 illustrates the same anatomical elements as depicted in the source image 302. However, regions of the image corresponding to these anatomical elements are more readily visible due to the application of appropriate configuration settings (e.g., brightness and contrast) to regions of the image. For example, fine detail on the patient's lungs 314 can be readily viewed within the merged image due to different brightness and contrast settings being applied than in the source image. An advantage of the merged image is readily discernable in that, while the detail of the lung region 314 is visible due to increased brightness and contrast settings in that region, detail of the bone and spine region 318 is also visible due to lower brightness and contrast settings being applied to that region. In previous implementations, application of the settings corresponding to the lung region 314 would make proper clinical analysis of the bone and spine region 318 impossible, and vice-versa. By providing the ability to adjust configuration settings on a region-by-region basis, embodiments provide an improved mechanism for viewing such medical image data. Similar benefits may be seen within the soft tissue region 312 and the heart region 316.

Exemplary Processes for Implementing Improved Image Processing and Viewing

Figure 4:
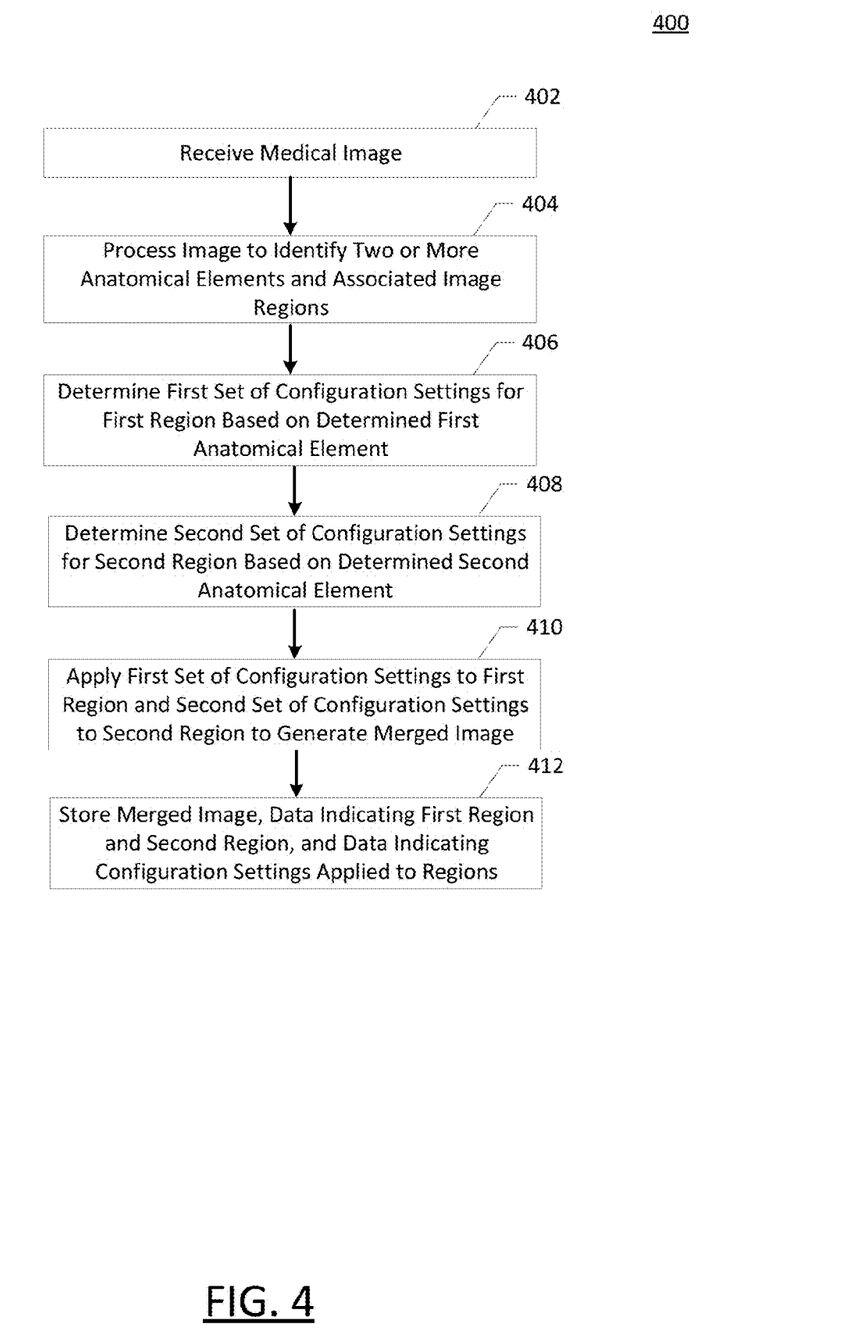
FIG. 4 is an illustration of a flow diagram illustrating an example of a process for generating a merged image in accordance with embodiments of the present invention.

FIG. 4 is a flow diagram depicting an exemplary process 400 for implementing an image processing technique as described above with respect to FIGS. 2-3B in accordance with embodiments of the present invention. These processes may be employed by an apparatus, such as the apparatus 100 described above, to generate a merged image from a source image by identifying anatomical elements within the source image and applying configuration settings to regions within the image corresponding to those anatomical elements. In this regard, the process describes algorithms that are implemented via hardware or software executing on hardware components of an apparatus to implement these tasks and other tasks related to implementation of improved image processing techniques. These algorithms may serve as means for implementing these tasks and other functions as described above and herein.

At action 402, a source image is received. As noted above, the source image may be in any suitable format for viewing, such as through the use of a PACS workstation. The image may, for example, be a DICOM image. The image may be stored in an archive or electronic health records system, received directly from a medical imaging system (e.g., directly from a capturing device), over a network, as an email attachment, or via any other process or mechanism.

At action 404, the image is processed to identify one or more anatomical elements within the image. Processing of the image in this manner includes the use of one or more algorithms for image analysis. These algorithms may, for example, utilize computer vision techniques to determine pixel regions of the source image that correspond to particular anatomical elements, and the type of anatomical elements depicted therein. These detected anatomical elements and the regions of the source image to which they correspond may be stored for later reference.

At action 406, a first set of configuration settings are identified for a region associated with a first anatomical element. The first set of configuration settings may be determined, for example, by performing a table lookup on a table of configuration settings indexed by anatomical element.

At action 408, a second set of configuration settings are identified for a region associated with a second anatomical element. The second set of configuration settings may be determined in a similar manner as the first set of configuration settings, such as by performing a similar table lookup. In some embodiments, as the user navigates through a series of images, the configuration settings applied to later images in a series may be derived from selections made for images earlier in the series. In this regard, image regions across images in a series may be mapped to one another such that adjustments to configuration settings in a first region in a first image may be mapped to a region of a second image when viewing the second image in a series.

At action 410, the first set of configuration settings are applied to the first region of the source image and the second set of configuration settings are applied to the second region of the source image to generate a merged image. In this manner, the merged image may have a first region that corresponds to a set of pixels visualized using the first set of configuration settings (e.g., base pixel intensity values modified by a first brightness and contrast values) and a second region that corresponds to a set of pixels visualized using the second set of configuration settings (e.g., base pixel values modified by the second brightness and contrast values). At action 412, the merged image is stored for later retrieval, viewing, or the like.

Some embodiments may also store information that defines the different regions of the merged image and the configuration settings used for visualization of each of the regions. Storage of this additional data may enable certain additional use cases. For example, some embodiments may provide an interface that allows a clinician to select a particular region via a user interface. Selection of that region may cause the configuration settings associated with that region to be applied across the entire image.

It will be understood that each element of the flowcharts, and combinations of elements in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 104 of an apparatus employing an embodiment of the present invention and executed by a processor 102 of the apparatus. As will be appreciated, any such computer program instructions may be loaded onto a computer or other programmable apparatus (e.g., hardware)

to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for implementing improved image processing techniques, the method comprising:
   receiving a source image;
   programmatically identifying a plurality of anatomical elements within the source image through use of a computer vision technique;
   determining a first region of the source image corresponding to a first anatomical element of the plurality of anatomical elements;
   determining a type of the first anatomical element using the computer vision technique;
   determining a second region of the source image corresponding to a second anatomical element of the plurality of anatomical elements;
   applying at least one first configuration setting to the first region, wherein the at least one first configuration setting is determined based, at least in part, on the determined type of the first anatomical element;
   applying at least one second configuration setting to the second region, the at least one second configuration setting different from the at least one first configuration setting;
   generating a merged image, wherein the merged image comprises the first region as visualized according to the at least one first configuration setting and the second region as visualized according to the at least one second configuration setting;
   displaying the merged image in an interface, wherein the interface comprises at least one interface control associated with each of the first region and the second region;
   receiving a selection of an interface control associated with the first region; and
   in response to receiving the selection of the interface control associated with the first region, applying the at least one first configuration setting to the entire merged image.

2. The method of claim 1, wherein determining the at least one first configuration setting based at least in part on the determined type of the first anatomical element comprises looking up the type of the first anatomical element in a database of configuration settings.

3. The method of claim 1, wherein the at least one first configuration setting comprises at least one of a brightness setting, a contrast setting, or a color correction setting.

4. The method of claim 1, wherein generating the merged image further comprises outputting the merged image via a viewer application.

5. The method of claim 1, wherein the merged image is output via a Picture Archiving and Communications System.

6. The method of claim 1, wherein the source image is a Digital Imaging and Communications in Medicine image.

7. The method of claim 1, further comprising storing the merged image in a memory.

8. The method of claim 7, further comprising storing data defining the first region and the second region and the data defining the configuration settings associated with the first region and the second region as metadata for the merged image.

9. An apparatus for implementing improved image processing techniques, the apparatus comprising a processor and a memory, the memory storing instructions that are executed by the processor to configure the apparatus to:
   receive a source image;
   programmatically identify a plurality of anatomical elements within the source image through use of a computer vision technique;
   determine a first region of the source image corresponding to a first anatomical element of the plurality of anatomical elements;
   determine a type of the first anatomical element using the computer vision technique;
   determine a second region of the source image corresponding to a second anatomical element of the plurality of anatomical elements;
   apply at least one first configuration setting to the first region, wherein the at least one first configuration setting is selected based, at least in part, on the type of the first anatomical element;

apply at least one second configuration setting to the second region, the at least one second configuration setting different from the at least one first configuration setting;

generate a merged image, wherein the merged image comprises the first region as visualized according to the at least one first configuration setting and the second region as visualized according to the at least one second configuration setting;

display the merged image in an interface, wherein the interface comprises at least one interface control associated with each of the first region and the second region;

receive a selection of an interface control associated with the first region; and in response to receiving the selection of the interface control associated with the first region, apply the at least one first configuration setting to the entire merged image.

10. The apparatus of claim 9, wherein selecting at least one first configuration setting based at least in part on the type of the first anatomical element comprises looking up the type of the first anatomical element in a database of configuration settings.

11. The apparatus of claim 9, wherein the at least one first configuration setting comprises at least one of a brightness setting, a contrast setting, or a color correction setting.

12. The apparatus of claim 9, wherein generating the merged image further comprises outputting the merged image via a viewer application.

13. The apparatus of claim 9, wherein the merged image is output via a Picture Archiving and Communications System.

14. The apparatus of claim 9, wherein the source image is a Digital Imaging and Communications in Medicine image.

15. The apparatus of claim 9, further configured to store the merged image in a memory.

16. A non-transitory computer readable storage medium comprising instructions that, when executed by a processor, cause the processor to implement improved image processing techniques by configuring the processor to:

receive a source image;

programmatically identify a plurality of anatomical elements within the source image through use of a computer vision technique;

determine a first region of the source image corresponding to a first anatomical element of the plurality of anatomical elements;

determine a type of the first anatomical element using the computer vision technique;

determine a second region of the source image corresponding to a second anatomical element of the plurality of anatomical elements;

apply at least one first configuration setting to the first region, wherein the at least one first configuration setting is selected based, at least in part, on the type of the first anatomical element;

apply at least one second configuration setting to the second region, the at least one second configuration setting different from the at least one first configuration setting;

generate a merged image, wherein the merged image comprises the first region as visualized according to the at least one first configuration setting and the second region as visualized according to the at least one second configuration setting;

display the merged image in an interface, wherein the interface comprises at least one interface control associated with each of the first region and the second region;

receive a selection of an interface control associated with the first region; and in response to receiving the selection of the interface control associated with the first region, apply the at least one first configuration setting to the entire merged image.

* * * * *